(12) United States Patent
Streeter et al.

(10) Patent No.: US 7,534,255 B1
(45) Date of Patent: *May 19, 2009

(54) LOW LEVEL LIGHT THERAPY FOR ENHANCEMENT OF NEUROLOGIC FUNCTION

(75) Inventors: Jackson Streeter, Reno, NV (US); Luis De Taboada, Carlsbad, CA (US)

(73) Assignee: PhotoThera, Inc, Carlsbad, CA (US)

( * ) Notice: Subject to any disclaimer, the term of this patent is extended or adjusted under 35 U.S.C. 154(b) by 814 days.

This patent is subject to a terminal disclaimer.

(21) Appl. No.: 10/764,986

(22) Filed: Jan. 26, 2004

Related U.S. Application Data

(60) Provisional application No. 60/537,190, filed on Jan. 19, 2004, provisional application No. 60/487,979, filed on Jul. 17, 2003, provisional application No. 60/442,693, filed on Jan. 24, 2003.

(51) Int. Cl.
 *A61N 5/06* (2006.01)
(52) U.S. Cl. .................................... 607/88; 128/898
(58) Field of Classification Search ................. 128/898; 607/88–94
 See application file for complete search history.

(56) References Cited

U.S. PATENT DOCUMENTS

| | | | |
|---|---|---|---|
| 3,735,755 A | 5/1973 | Eggleton et al. |
| 3,810,367 A | 5/1974 | Peterson |
| 4,315,514 A | 2/1982 | Drewes et al. |
| 4,343,301 A | 8/1982 | Indech |
| 4,630,273 A | 12/1986 | Inoue et al. |
| 4,633,872 A | 1/1987 | Chaffee et al. |
| 4,669,466 A | 6/1987 | L'Esperance |
| 4,671,285 A * | 6/1987 | Walker .................... 607/89 |
| 4,798,215 A | 1/1989 | Turner |

(Continued)

FOREIGN PATENT DOCUMENTS

EP 0 130 950 11/1990

(Continued)

OTHER PUBLICATIONS

U.S. Appl. No. 10/682,379, filed Oct. 9, 2003, De Taboada et al.

(Continued)

*Primary Examiner*—Henry M Johnson, III
(74) *Attorney, Agent, or Firm*—Knobbe, Martens, Olson & Bear, LLP

(57) ABSTRACT

Therapeutic methods for enhancing neurologic function such as may be desired in individuals having motor and/or cognitive impairment, including that resulting from Alzheimer's disease, dementia, head trauma, mental disease such as depression, stroke and neurodegeneration, as well as in healthy individuals are described, the methods including delivering a cognitive enhancing effective amount of light energy having a wavelength in the visible to near-infrared wavelength range to a target area of the brain. The neurologic function enhancing effective amount of light energy, in accordance with a preferred embodiment, is a predetermined power density ($mW/cm^2$) at the level of the brain tissue being treated, and is delivered by determining a surface power density of the light energy that is sufficient to deliver the predetermined power density of light energy to the target brain tissue. In one embodiment, progenitor cells are treated using light energy and implanted into the central nervous system of a patient.

22 Claims, 1 Drawing Sheet

U.S. PATENT DOCUMENTS

| | | | |
|---|---|---|---|
| 4,846,196 A | 7/1989 | Wiksell et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,054,470 A | 10/1991 | Fry et al. |
| 5,150,704 A | 9/1992 | Tatebayashi et al. |
| 5,259,380 A | 11/1993 | Mendes et al. |
| 5,267,294 A | 11/1993 | Kuroda et al. |
| 5,282,797 A | 2/1994 | Chess |
| 5,358,503 A | 10/1994 | Bertwell et al. |
| 5,401,270 A | 3/1995 | Muller et al. |
| 5,441,495 A | 8/1995 | Liboff et al. |
| 5,445,146 A | 8/1995 | Bellinger |
| 5,445,608 A | 8/1995 | Chen et al. |
| 5,464,436 A | 11/1995 | Smith |
| 5,501,655 A | 3/1996 | Rolt et al. |
| 5,511,563 A | 4/1996 | Diamond |
| 5,540,737 A | 7/1996 | Fenn |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,728,090 A | 3/1998 | Martin et al. |
| 5,755,752 A | 5/1998 | Segal |
| 5,817,008 A | 10/1998 | Rafert et al. |
| 5,842,477 A | 12/1998 | Naughton et al. |
| 5,843,073 A | 12/1998 | Sinofsky |
| 5,849,585 A | 12/1998 | Mather et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Seliktar et al. |
| 5,954,762 A | 9/1999 | Di Mino et al. |
| 5,983,141 A | 11/1999 | Sluijter et al. |
| 5,989,245 A | 11/1999 | Prescott |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Di Mino et al. |
| 6,156,028 A | 12/2000 | Prescott |
| 6,179,771 B1 | 1/2001 | Mueller |
| 6,187,210 B1 | 2/2001 | Lebouitz et al. |
| 6,198,958 B1 | 3/2001 | Ives et al. |
| 6,210,317 B1 | 4/2001 | Bonlie |
| 6,214,035 B1 | 4/2001 | Streeter |
| 6,221,095 B1 | 4/2001 | Van Zuylen et al. |
| 6,267,780 B1 | 7/2001 | Streeter |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,312,451 B1 | 11/2001 | Streeter |
| 6,344,050 B1 | 2/2002 | Chen |
| 6,358,272 B1 | 3/2002 | Wilden |
| 6,363,285 B1 | 3/2002 | Wey |
| 6,364,907 B1 | 4/2002 | Obochi et al. |
| 6,379,295 B1 | 4/2002 | Woo |
| 6,395,016 B1 | 5/2002 | Oron et al. |
| 6,397,107 B1 | 5/2002 | Lee et al. |
| 6,402,678 B1 | 6/2002 | Fischell et al. |
| 6,421,562 B1 | 7/2002 | Ross |
| 6,443,974 B1 | 9/2002 | Oron et al. |
| 6,443,978 B1 | 9/2002 | Zharov |
| 6,471,716 B1 | 10/2002 | Pecukonis |
| 6,514,220 B2 | 2/2003 | Melton, Jr. et al. |
| 6,537,304 B1 | 3/2003 | Oron |
| 6,551,308 B1 | 4/2003 | Muller et al. |
| 6,663,659 B2 | 12/2003 | McDaniel et al. |
| 2001/0044623 A1 | 11/2001 | Chen |
| 2002/0068927 A1 | 6/2002 | Prescott |
| 2002/0087205 A1 | 7/2002 | Chen |
| 2002/0123781 A1 | 9/2002 | Shanks et al. |
| 2002/0188334 A1 | 12/2002 | Carlgren |
| 2002/0198575 A1 | 12/2002 | Sullivan |
| 2003/0109906 A1 * | 6/2003 | Streeter ............... 607/88 |
| 2003/0125782 A1 | 7/2003 | Streeter |
| 2003/0144712 A1 | 7/2003 | Streeter |
| 2003/0167080 A1 | 9/2003 | Hart et al. |
| 2003/0212442 A1 | 11/2003 | Streeter |
| 2003/0216797 A1 | 11/2003 | Oron |
| 2004/0014199 A1 | 1/2004 | Streeter |
| 2004/0044384 A1 | 3/2004 | Leber et al. |
| 2004/0132002 A1 | 7/2004 | Streeter |
| 2004/0220513 A1 | 11/2004 | Streeter |
| 2004/0260367 A1 | 12/2004 | De Taboada et al. |
| 2005/0009161 A1 | 1/2005 | Streeter |
| 2005/0107851 A1 | 5/2005 | De Taboada et al. |

FOREIGN PATENT DOCUMENTS

| | | |
|---|---|---|
| EP | 0 763 371 A2 | 3/1997 |
| EP | 0 783 904 A2 | 7/1997 |
| EP | 1 226 787 A2 | 7/2002 |
| JP | 04023634 | 2/1992 |
| WO | WO 96/36396 | 11/1996 |
| WO | WO 98/04321 | 2/1998 |
| WO | WO 98/22573 | 5/1998 |
| WO | WO 99/42178 | 8/1999 |
| WO | WO 99/62599 A1 | 12/1999 |
| WO | WO 9962599 A1 * | 12/1999 |
| WO | WO 00/35534 A1 | 6/2000 |
| WO | WO 2005/025672 A1 | 3/2005 |

OTHER PUBLICATIONS

U.S. Appl. No. 10/448,262, filed May. 29, 2003, Oron et al.
U.S. Appl. No. 10/612,709, filed Jul. 2, 2003, Streeter.
U.S. Appl. No. 10/723,171, filed Nov. 26, 2003, Streeter.
U.S. Appl. No. 10/764,986, filed Jan. 6, 2004, Streeter.
PCT/US03/00747 International Search Report.
PCT/US02/36808 International Search Report.
PCT/CA99/00156 International Search Report.
PCT/US04/029724 International Search Report.
PCT/US2005/004873 Partial ISR dated Jun. 16, 2005, Publication date Feb. 11, 2005, Photothera, Inc.
*Optical Properties of Tissues with Strong (Multiple) Scattering*, source unknown.
Van Brugel, Hans H.F.I., et al., *Power Density and Exposure Time of He-Ne Laster Irradiation ar eMore Important than Total Energy Dose in Photo-Biomoducation of Human Fibroblasts* In Vitro, 1992, Wiley-Liss, Inc.
Agov, B.S., et al., On the mechanism of therapeutic action of helium-neon laser in ischemic heart disease, *Klin Med (Mosc)*, 1985, pp. 102-105 (Abstract only).
Arvidsson, Andreas, et al., Neuronal replacement from endogenous precursors in the adult rat brain after stroke, *Nature Medicine*, vol. 8, No. 9, Sep. 2002, pp. 963-970.

Brazzle, John, et al., Active Microneedles with Integrated Functionality, *Technical Digest of the 2000 Solid-State Sensor and Actuator Workshop*, Department of Bioengineering, University of Utah, Salt Lake City, Utah 84112 (five pages).

Brill, G.E., et al., *Modifying influence of low level laser irradiation on the relationships in endothelial cell—blood platelet system*, 10th Congress of the European Society for Photobiology, Vienna, Austria (one page).

Byrnes, K.R., et al., Light Therapy Promotes Axonal Regeneration After Acute Spinal Cord Injury in Adult Rats, Program No. 275.2, *Society for Neuroscience*, 2003, Abstract.

Cohen, Michael A., *Method of Forming Microneedles and other Micron-Scale Transdermal Probes*, Office of Technology Licensing, University of California, Berkeley, http://otl.berkeley.edu/technology/inventiondetail.php/1000335, Abstract (two pages).

Dirnagl, Ulrich, et al., Pathobiology of ischaemic stroke: an integrated view, *TINS*, vol. 22, No. 9, 1999, pp. 391-397.

Eells, J.T., et al., Therapeutic photobiomodulation for methanol-induced retinal toxicity, *Proceedings National Academy of Science (PNAS)*, vol. 100, No. 6, Mar. 18, 2003, pp. 3439-3444.

Elimadi, Aziz, et al., Trimetazidine Counteracts the Hepatic Injury Associated with Ischemia-Reperfusion by Preserving Michondrial Function, *Journal of Pharmacology and Experimental Therapeutics*, vol. 286, No. 1, 1998, pp. 23-28.

Gage, Fred H., Brain, Repair Yourself, *Scientific American*, Sep. 2003, pp. 47-53.

Gasparyan, Levon V., et al., *Low Level Laser Therapy of Male Genital Tract Chronic Inflammations*, WALT 2-nd Congress (Kansas City, USA), 1998 (two pages).

Gasparyan, L.V., et al., *The influence of LED irradiation at different wavelengths on functional activity of blood platelets*, 10th Congress of the European Society for Photobiology, Vienna, Austria, 2003 (one page).

Gasparyan, L.V., et al., *The influence of LED irradiation at different wavelengths with antioxidants on functional activity of blood platelets*, Laser, Florence, 2003 (one page).

Gasparyan, Levon V., Biochemical and Biophysical Effects of Low Level Laser Irradiation, *MAL 2000*, Helsinki, Finland (three pages).

Gasparyan, Levon V., Experience of Russian (former USSR) Scientists in LLLT and UV Blood Irradiation, *MAL 2000*, Helsinki, Finland (four pages).

Gasparyan, Levon V., *Investigation of Sensations, Associated with Laser Blood Irradiation*, WALT 2-nd Congress (Kansas City, USA), 1998 (two pages).

Gasparyan, Levon V., Millimeter Wave Therapy, *MAL 2000*, Helsinki, Finland (three pages).

Gross, Garrett J., et al., *Mechanisms of Postischemic Contractile Dysfunction*, Myocardial Protection From Surgical Ischemic-Reperfusion Injury, An International Symposium, Asheville, North Carolina, Sep. 21-24, 1997, pp. 1898-1904.

Hammon, John W. Jr, MD, et al., *Myocardial Protection Form Surgical Ischemic-Reperfusion Injury*, Ann Thorac Surg 1999:68:1897.

Iadecola, Costantino, et al., Inhibition of inducible nitric oxide synthase ameliorates ischemic damage, *Am. J. Physiol.*, vol. 268, 1995, pp. R286-R292.

Karu, Tiina, Mechanisms of Low-Power Laser Light Action on Cellular Level, *Effects of Low-Power Light on Biological Systems V*, Proceedings of SPIE, Jul. 7, 2000, vol. 4159, 2000.

Karu, T.I., *Low power laser therapy*, in Biomedical Photonics Handbook, Ch. 48, Editor-in-Chief Tuan Vo-Dinh, Boca Raton, CRC Press, 2003.

Karu, Tiina, *Mechanisms of interaction of monochromatic visible light with cells*, Proc. SPIE, vol. 2630, pp. 2-9.

Karu, Tiina, Photobiological Fundamentals of Low Power Laser Therapy, *IEEE Journal of Quantum Electronics*, vol. QE-23, No. 10, Oct. 1987, pp. 1703-1717.

*The Laser Exchange: Delivering the medicine of the future*, www.laserexchange.co.uk/laser-therapy/ultrasoun.htm, 42 pages.

Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Lasers in Surgery and Medicine*, vol. 31, 2002, pp. 283-288.

Minoru, Asahi, et al, *Expression of Interleukin-1[beta] Converting Enzyme Geme Family and bcl-2 Gene Family in the Rat Brain Following Permanent Occlusion of the Middle Cerebral Artery*, Journal of Cerebral Blood Flow & Metabolism, vol. 17(1), Jan. 1997, pp. 11-18.

Mochizuki-Oda, Noriko, et al., Effects of near-infra-red laser irradiation on adenosine triphosphate and adenosine diphosphate contents of rat brain tissue, *Neuroscience Letters 323*, May 3, 2002, pp. 207-210.

Nishioka, Norman S., et al., Reflection and Transmission of Laser Light From the Esophagus: The Influence of Incident Angle, *Gastroenterology*, vol. 94, 1988, pp. 1180-1185.

Olesin, Al, et al., Laser irradiation of venous blood for production of reperfusion syndrome in myocardial infarction, *Patologisheskaia fiziologiia*, 1992 (Abstract only).

Oron, Uri, et al., Attenuation of Infarct Size in Rats and Dogs after Myocardial Infarction by Low-Energy Laser Irradiation, *Lasers in Surgery and Medicine*, vol. 28, 2001, pp. 204-211.

Oron, Uri, et al., Low-Energy Laser Irradiation Reduces Formation of Scar Tissue After Myocardial Infarction in Rats and Dogs, *Circulation*, vol. 103, Jan. 16, 2001, pp. 296-301.

Park, James L., Ph.D., et al., Mechanisms of Myocardial Reperfusion Injury, *The Annals of Thoracic Surgery*, Official Journal of The Society of Thoracic Surgeons and the Southern Thoracic Surgical Association, vol. 68, No. 5, Nov. 1999, pp. 1905-1912.

Semenza, Gregg L., et al., Regulation of Mammalian $O_2$ Homeostasis by Hypoxia-Inducible Factor 1, *Ann. Rev. Cell Dev. Biol.*, vol. 15, 1999, pp. 551-578.

Stys, Peter K., Anoxis and Ischemic Injury of Myelinated Axons in CNS White Matter: From Mechanistic Concepts to Therapeutics, *J. Cereb Blood Flow Metab.*, vol. 18, No. 1, Jan. 1998, pp. 2-25.

*Is LLLT Different from Ultrasound?*, http://www.thorlaser.com/LLLT/is-LLLT-diff-from-ultrasound.htm, 2 pages.

Product List, Tho, lllt, LLLT, *Low Level Laser Therapy, Laz.*, http://www.thorlaser.com/prodlist/index.html, Oct. 6, 1999, pp. 1-4.

Specifications, Thor, lllt, LLLT, *Low Level Laser Therapy, low level laser therapy*, http://www.thorlaser.com/specs, Oct. 6, 1999, pp. 1-2.

100mW, Thor, lllt, LLLT, *Low Level Laser Therapy, low level laser therapy, Lazer, Thorl.*, http://www.thorlaser.com/_specs/_100m_W.html, Oct. 6, 1999, p. 1.

200mW, Thor, lllt, LLLT, *Low Level Laser Therapy, low level laser therapy, Lazer, Thorl.*, http://www.thorlaser.com/_specs/200m_W.html, Oct. 6, 1999, p. 1.

500mW, Thor, lllt, LLLT, *Low Level Laser Therapy, low level laser therapy, Lazer, Thorl.*, http://www.thorlaser.com/_specs/500m_W.html, Oct. 6, 1999, p. 1.

200mW, Thor, lllt, LLLT, *Low Level Laser Therapy, low level laser therapy, Laser, Thorl.*, http://www.thorlaser.com/_specs/200m_W650nm.html, Oct. 6, 1999, p. 1.

680nm Probe, Thor, lllt, LLLT, *Low Level Laser Therapy, low level laser therapy, Laser*, http://www.thorlaser.com/_specs/680.html, Oct. 6, 1999, p. 1.

Toon, John, Taking the "Ouch" Out of Needles: Arrays of Micron-Scale "Microneedles" Offer New Technique for Drug Delivery, *Georgia Tech Research News*, Jun. 22, 1998 (three pages).

Toricelli, P., et al., Laser Biostimulation of cartilage: in vitro evaluation, *Biomed Pharmacother* 2001, vol. 55, pp. 117-120.

Tuchin, Valery, *Tissue Optics: Light Scattering Methods and Instruments for Medical Diagnosis*, SPIE Press, Tutorial Texts in Optical Engineering, vol. TT38, 2000, pp. 3-11.

Tunér, Jan, et al., Low Level Laser Therapy, *Clinical Practice and Scientific Background*, Prima Books in Sweden AB, 1999, pp. 1-9, 45-58, 59-109, 62-114; 113-116, 118, 132-134, 134-135; 149-151; 151-156; 185; 334-364.

Wong-Riley, Margaret T.T., et al., Light-emitting diode treatment reverses the effect of TTX on cytochrome oxidase in neurons, *NeuroReport*, vol. 12, No. 14, Oct. 8, 2001, pp. 3033-3037.

Yaakobi, Tali, et al., Long-term effect of low energy laser irradiation on infarction and reperfusion injury in the rate heart, *J. Appl. Physiol.*, vol. 90, 2001, pp. 2411-2419.

* cited by examiner

LOW LEVEL LIGHT THERAPY FOR ENHANCEMENT OF NEUROLOGIC FUNCTION

RELATED APPLICATION DATA

This application claims priority under 35 U.S.C. § 119(e) to U.S. Provisional Patent Application Nos. 60/442,693, filed Jan. 24, 2003, 60/487,979, filed Jul. 17, 2003, and 60/537,190, entitled Method for the Treatment of Depression, filed Jan. 19, 2004, all of which are hereby incorporated by reference in their entireties.

FIELD OF THE INVENTION

The present invention relates to methods for enhancing neurologic function such as may be desired in individuals having a loss of such function, including motor function and cognitive function, including that resulting from Alzheimer's disease, dementia, heat stroke, head trauma, depression, stroke, and neurodegeneration, as well as in healthy individuals, using light therapy.

BACKGROUND OF THE INVENTION

Dementia is characterized as the loss of cognitive function having a severity so as to interfere with a person's daily activities. Cognitive function includes activities such as knowing, thinking, learning, memory, perception, and judging. Symptoms of dementia can also include changes in personality, mood, and behavior of the subject.

Dementia is a collection of symptoms that can be caused by any of a variety of diseases or conditions; it is not itself a disease. Although, in some cases, dementia can be cured by curing the underlying disease (e.g. infection, nutritional deficiency, tumor), in most cases dementia is considered incurable.

Dementia is considered a late-life disease because it tends to develop mostly in elderly people. About 5-8% of all people over the age of 65 have some form of dementia, and this number doubles every five years above that age. It is estimated that as many as half of people in their 80s suffer from some form of dementia. The most common cause of dementia is Alzheimer's disease, which affects about 4 million Americans and appears to be increasing in frequency more than most other types of dementia. Other causes of dementia include AIDS or HIV infection, Creutzfeldt-Jakob disease, head trauma (including single-event trauma and long term trauma such as multiple concussions or other traumas which may result from athletic injury), Lewy body disease, Pick's disease, Parkinson's disease, Huntington's disease, drug or alcohol abuse, brain tumors, hydrocephalus, and kidney or liver disease.

Furthermore, people suffering from mental diseases or disorders can suffer from varying levels of diminishment of cognitive function that do not rise to the level of dementia. Additionally, generally healthy individuals may also perceive some loss of cognitive function, most commonly a reduction in the function of memory. Loss or diminishment of memory may occur in any of the four commonly designated phases of memory, namely learning, retention, recall and recognition, and may be related to immediate memory, recent memory or remote memory. Loss of motor function may occur as a result of any of a number of causes, including many of those discussed above for which there is also a loss of cognitive function.

High energy laser radiation is now well accepted as a surgical tool for cutting, cauterizing, and ablating biological tissue. High energy lasers are now routinely used for vaporizing superficial skin lesions and, to make deep cuts. For a laser to be suitable for use as a surgical laser, it must provide laser energy at a power sufficient to heart tissue to temperatures over 50° C. Power outputs for surgical lasers vary from 1-5 W for vaporizing superficial tissue, to about 100 W for deep cutting.

In contrast, low level laser therapy involves therapeutic administration of laser energy to a patient at vastly lower power outputs than those used in high energy laser applications, resulting in desirable biostimulatory effects while leaving tissue undamaged. For example, in rat models of myocardial infarction and ischemia-reperfusion injury, low energy laser irradiation reduces infarct size and left ventricular dilation, and enhances angiogenesis in the myocardium. (Yaakobi et al., *J. Appl. Physiol.* 90, 2411-19 (2001)). Low level laser therapy has been described for treating pain, including headache and muscle pain, and inflammation.

SUMMARY OF THE INVENTION

The low level light therapy methods for enhancing neurologic function are based in part on the new and surprising discovery that power density (i.e., power per unit area) of the light energy applied to tissue appears to be a very important factor in determining the relative efficacy of low level light therapy, and particularly with respect to enhancing the function of neurons in both healthy and diseased states.

In accordance with one embodiment there are provided methods directed toward the enhancement of neurologic function in a subject. The methods include delivering a neurologic enhancing effective amount of a light energy having a wavelength in the visible to near-infrared wavelength range to at least one area of the brain of a subject. In a preferred embodiment delivering the neurologic function enhancing effective amount of light energy includes delivering a predetermined power density of light energy through the skull to the target area of the brain and/or delivering light energy through the skull to at least one area of the brain of a subject, wherein the wavelength, power density and amount of the light energy delivered are sufficient to cause an enhancement of neurologic functioning.

In accordance with one embodiment there is provided a method for preventing heat stroke in a subject. The term "preventing" in this context includes reducing the severity of a later heat stroke in a subject that has undergone treatment, reducing the incidence of heat stroke in individuals who have undergone treatment, as well as reducing the likelihood of onset heat stroke in a subject that has undergone treatment. The method includes delivering light energy having a wavelength in the visible to near-infrared wavelength range through the skull to at least one area of the brain of a subject, wherein the wavelength, power density and amount of the light energy delivered are sufficient to prevent, reduce the severity, or reduce the incidence of heat stroke in the subject.

In preferred embodiments, the target area of the brain may be all of the brain or a specific area of the brain including, but not limited to, an area associated with a particular cognitive or motor function, an area exhibiting neurodegeneration, the cortex, and/or an area that has been affected by trauma. The subject may have a cognitive or motor impairment such as from neurodegeneration or the subject may be normal.

In one embodiment, the predetermined power density is a power density of at least about 0.01 mW/cm$^2$. The predetermined power density in preferred embodiments is typically selected from the range of about 0.01 mW/cm² to about 100 mW/cm², including from about 0.01 mW/cm² to about 15 mW/cm² and from about 2 mW/cm² to about 50 mW/cm². In some embodiments, power densities above or below these values may be used.

In preferred embodiments, the methods encompass using light energy having a wavelength of about 630 nm to about 904 nm, and in one embodiment the light energy has a wavelength of about 780 nm to about 840 nm. The light energy is preferably from a coherent source (i.e. a laser), but light from non-coherent sources may also be used.

In some preferred embodiments, the methods encompass placing a light source in contact with a region of skin that is either adjacent an area of the brain in which treatment is desired, contralateral to such area, or a combination of the foregoing, and then administering the light energy, including the neurologic function enhancing effective amount of light energy, as may be measured by power density, to the area of the brain. In delivering the light, the power density may be a predetermined power density. Some preferred methods encompass determining a surface power density of the light energy sufficient for the light energy to penetrate the skull. The determination of the required surface power density, which is relatively higher than the power density to be delivered to the brain tissue being treated, takes into account factors that attenuate power density as it travels through tissue, including skin pigmentation, and location of the brain area being treated, particularly the distance of the brain area from the skin surface where the light energy is applied.

In accordance with another embodiment, there is provided a method of increasing the production of ATP by neurons to increase neurologic function. The method comprises irradiating neurons with light energy having a wavelength in the near infrared to visible portion of the electromagnetic spectrum for at least about 1 second, where the power density of said light energy at the neurons is at least about 0.01 mW/cm².

In accordance with another embodiment, there is provided a method for treating damage or illness in the central nervous system in a mammal or human, comprising delivering an effective amount of light energy to an in vitro culture comprising progenitor cells, and implanting the cells into the central nervous system of a mammal or human, wherein delivering an effective amount of light energy includes delivering light having a wavelength in the visible to near-infrared wavelength range and a power density of at least about 0.01 mW/cm² to the cells in culture.

DETAILED DESCRIPTION OF THE PREFERRED EMBODIMENTS

The low level light therapy methods for enhancing neurologic function and preventing, reducing the severity or reducing the incidence of heat stroke described herein may be practiced using, for example, a low level laser therapy apparatus such as that shown and described in U.S. Pat. No. 6,214,035, U.S. Pat. No. 6,267,780, U.S. Pat. No. 6,273,905 and U.S. Pat. No. 6,290,714, which are all herein incorporated by reference together with references contained therein.

Figure 1:
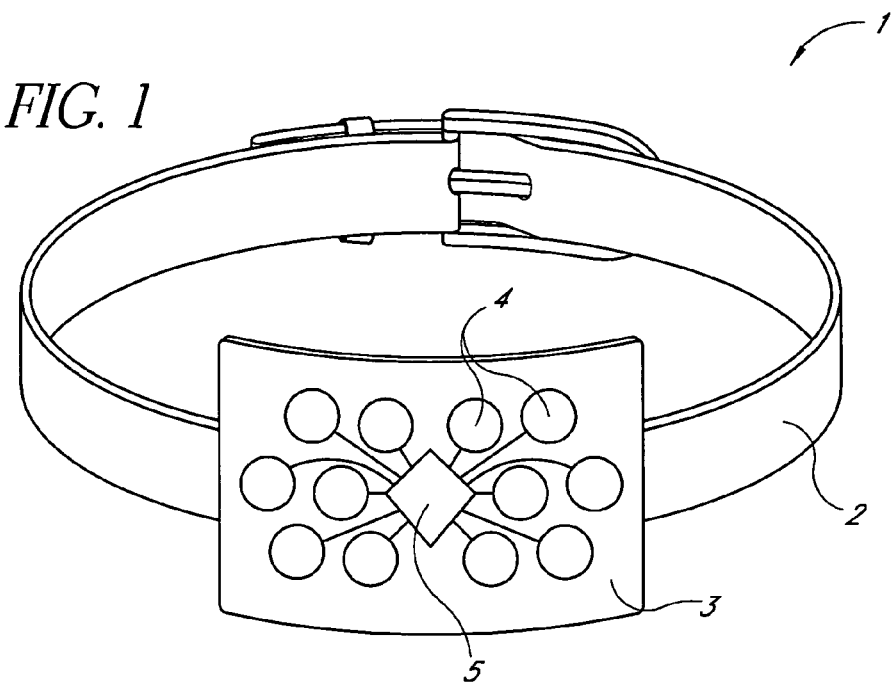
FIG. 1 is a perspective view of a first embodiment of a light therapy device.

Another suitable light therapy apparatus is that illustrated in FIG. 1. The illustrated device 1 includes a flexible strap 2 with a securing means, the strap adapted for securing the device over an area of the subject's body, one or more light energy sources 4 disposed on the strap 2 or on a plate or enlarged portion of the strap 3, capable of emitting light energy having a wavelength in the visible to near-infrared wavelength range, a power supply operatively coupled to the light source or sources, and a programmable controller 5 operatively coupled to the light source or sources and to the power supply. Based on the surprising discovery that control or selection of power density of light energy is an important factor in determining the efficacy of light energy therapy, the programmable controller is configured to select a predetermined surface power density of the light energy sufficient to deliver a predetermined subsurface power density to a body tissue to be treated beneath the skin surface of the area of the subject's body over which the device is secured.

The light energy source or sources are capable of emitting the light energy at a power sufficient to achieve the predetermined subsurface power density selected by the programmable controller. It is presently believed that tissue will be most effectively treated using subsurface power densities of light of at least about 0.01 mW/cm² and up to about 100 mW/cm², including about 0.05, 0.1, 0.5, 1, 5, 10, 15, 20, 30, 40, 50, 60, 70, 80, and 90 mW/cm². In one embodiment, power densities of about 20 mW/cm² to about 50 mW/cm² are used. To attain subsurface power densities within these stated ranges, taking into account attenuation of the energy as it travels through bone, body tissue, and fluids from the surface to the target tissue within the brain or on the surface of the brain, surface power densities of from about 100 mW/cm² to about 500 mW/cm² will typically be required, but also possibly to a maximum of about 1000 mW/cm². To achieve such surface power densities, preferred light energy sources, or light energy sources in combination, are capable of emitting light energy having a total power output of at least about 25 mW to about 500 mW, including about 30, 50, 75, 100, 150, 200, 250, 300, and 400 mW, but may also be up to a maximum of about 1000 mW. It is believed that the subsurface power densities of at least about 0.01 mW/cm² and up to about 100 mW/cm² in terms of the power density of energy that reaches the subsurface tissue are especially effective at producing the desired biostimulative effects on tissue being treated.

The strap is preferably fabricated from an elastomeric material to which is secured any suitable securing means, such as mating Velcro strips, snaps, hooks, buttons, ties, or the like. Alternatively, the strap is a loop of elastomeric material sized appropriately to fit snugly over a particular body part, such as a particular arm or leg joint, or around the chest or head. The precise configuration of the strap is subject only to the limitation that the strap is capable of maintaining the light energy sources in a select position relative to the particular area of the body or tissue being treated. In an alternative embodiment, a strap is not used and instead the light source or sources are incorporated into or attachable onto a light cap which fits securely over the head thereby holding the light source or sources in proximity to the patient's head for treatment. The light cap is preferably constructed of a stretchable fabric or mesh comprising materials such as Lycra or nylon. The light source or sources are preferably removably attached to the cap so that they may be placed in the position needed for treatment of any portion of the brain.

In the exemplary embodiment illustrated in FIG. 1, a light therapy device includes a flexible strap and securing means such as mating Velcro strips configured to secure the device around the head of the subject. The light source or sources are disposed on the strap, and in one embodiment are enclosed in a housing secured to the strap. Alternatively, the light source or sources are embedded in a layer of flexible plastic or fabric that is secured to the strap. In any case, the light sources are secured to the strap so that when the strap is positioned around a body part of the patient, the light sources are positioned so that light energy emitted by the light sources is directed toward the skin surface over which the device is secured. Various strap configurations and spatial distributions of the light energy sources are contemplated so that the device can be adapted to treat different tissues in different areas of the body.

Figure 2:
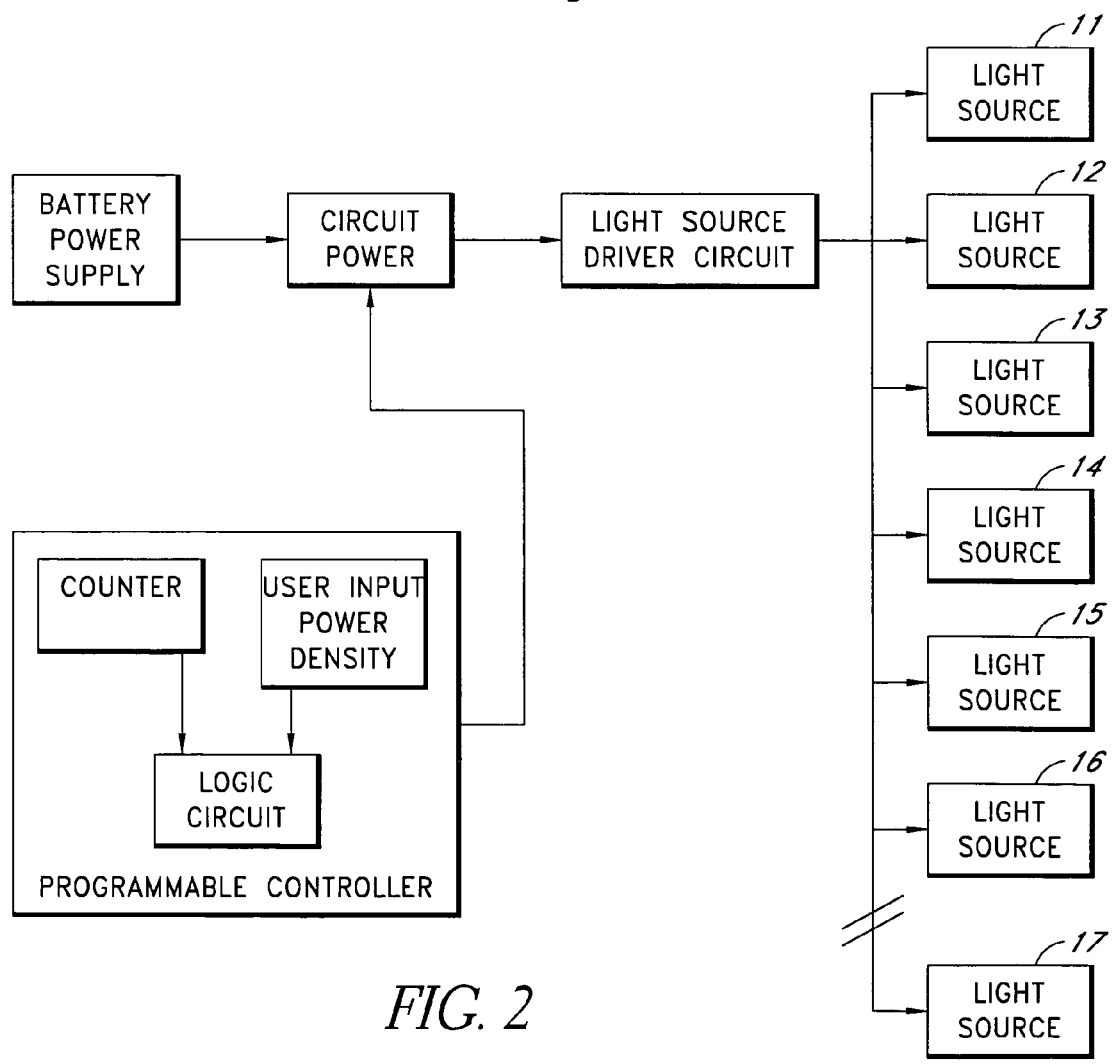
FIG. 2 is a block diagram of a control circuit for the light therapy device, according to one embodiment of the invention.

FIG. 2 is a block diagram of a control circuit according to one embodiment of the light therapy device. The programmable controller is configured to select a predetermined surface power density of the light energy sufficient to deliver a predetermined subsurface power density, preferably about 0.01 mW/cm$^2$ to about 100 mW/cm$^2$, including about 0.01 mW/cm$^2$ to about 15 mW/cm$^2$ and about 20 mW/cm$^2$ to about 50 mW/cm$^2$ to the infarcted area of the brain. The actual total power output if the light energy sources is variable using the programmable controller so that the power of the light energy emitted can be adjusted in accordance with required surface power energy calculations as described below.

Suitable for the methods described herein is a low level light apparatus including a handheld probe for delivering the light energy. The probe includes a light source of light energy having a wavelength in the visible to near-infrared wavelength range, i.e., from about 630 to about 904 nm, preferably about 780 nm to about 840 nm, including about 790, 800, 810, 820, and 830 nm. Preferred probes include, for example, a single source or laser diode that provides about 25 mW to about 500 mW of total power output, and multiple sources or laser diodes that together are capable of providing at least about 25 mW to about 500 mW of total power output. Probes and sources having power capacities outside of these limits may also be used in the methods according to preferred embodiments. The actual power output is variable using a control unit electronically coupled to the probe, so that power of the light energy emitted can be adjusted in accordance with required power density calculations as described below. In one embodiment, the diodes used are continuously emitting GaAlAs laser diodes having a wavelength of about 830 nm. In another embodiment, a laser source is used having a wavelength of about 808 nm. It has also been found that an intermediate wavelength of about 739 nm appears to be suitable for penetrating the skull, although other wavelengths are also suitable and may also be used.

Other preferred devices for use with the methods disclosed herein include those disclosed in U.S. patent application Ser. No. 10/682,379, filed Oct. 9, 2003, which is incorporated by reference in its entirety.

Preferred methods are based at least in part on the finding that given a select wave of light energy it is the power density of the light energy (i.e., light intensity or power per unit area, in W/cm$^2$) delivered to tissue, and not the power of the light source used nor the dosage of the energy used per se, that appears to be an important factor in determining the relative efficacy of low level light therapy. In the methods described herein, power density as delivered to a target area of the brain appears to be an important factor in using low level light therapy to achieve the desired clinical results. Without being bound by theory, it is believed that light energy delivered within a certain range of power densities provides the required biostimulative effect on the intracellular environment, such that the function of previously nonfunctioning or poorly functioning mitochondria in neurons is enhanced so as to return to a more normal state and the functioning of normally functioning mitochondria in neurons is enhanced to achieve better than normal functioning as well as to help the tissue be more resistant to the effects of excessive heat so as to prevent heat stroke or at least to reduce its incidence or severity.

The term "neurodegeneration" refers to the process of cell destruction resulting from primary destructive events such as stroke or trauma, and also secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms may contribute to forming a "zone of danger" for neurons, wherein the neurons in the zone have at least temporarily survived the primary destructive event, but are at risk of dying due to processes having delayed effect.

The term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

The term "cognitive function" as used herein refers to cognition and cognitive or mental processes or functions, including those relating to knowing, thinking, learning, perception, memory, and judging. Diseases or conditions affecting cognitive function include Alzheimer's disease, dementia, head trauma, stroke, depression and other mental diseases which cause disruption in cognitive function, and neurodegeneration.

The term "motor function" as used herein refers to those bodily functions relating to muscular movements, primarily conscious muscular movements, including motor coordination, performance of simple and complex motor acts, and the like.

The term "neurologic function" as used herein includes both cognitive function and motor function.

The terms "cognitive enhancement" and "motor enhancement" as used herein refer to the improving or heightening of cognitive function and motor function, respectively.

The term "neurologic enhancement" as used herein includes both cognitive enhancement and motor enhancement.

The term "neuroprotective effective" as used herein refers to a characteristic of an amount of light energy, wherein the amount is a power density of the light energy measured in mW/cm$^2$. The amount of light energy achieves the goal of preventing, avoiding, reducing or eliminating neurodegeneration, which should result in cognitive enhancement and/or motor enhancement.

The term "neurologic function enhancement effective" as used herein refers to a characteristic of an amount of light energy, wherein the amount is a power density of the light energy measured in mW/cm². The amount of light energy achieves the goal of neuroprotection, motor enhancement and/or cognitive enhancement.

Thus, a method for the enhancement of neurologic function in a subject involves delivering a neurologic function enhancement effective amount of light energy having a wavelength in the visible to near-infrared wavelength range to a target area of the brain of the subject. In a preferred embodiment, delivering the neurologic function enhancement effective amount of light energy includes selecting a surface power density of the light energy sufficient to deliver such predetermined power density of light energy to the target area of the brain. Likewise, a method for preventing, reducing the severity of a later heat stroke in a subject, reducing the incidence of future heat stroke, and/or reducing the likelihood of onset heat stroke in a subject includes delivering light energy having a wavelength in the visible to near-infrared wavelength range and a predetermined power density through the skull to at least one area of the brain of a subject, wherein the wavelength, power density and amount of the light energy delivered are sufficient to prevent, reduce the severity, or reduce the incidence of heat stroke in the subject.

Preferably, the predetermined power density to be delivered to the tissue in accordance with the above methods is selected to be at least about 0.01 mW/cm². In one embodiment, the predetermined power density is selected from the range of about 0.01 mW/cm² to about 100 mW/cm². To deliver the predetermined power density at the level of the brain tissue, a required, relatively greater surface power density of the light energy is calculated taking into account attenuation of the light energy as it travels from the skin surface through various tissues including skin, bone and brain tissue. Factors known to affect penetration and to be taken into account in the calculation include skin pigmentation, the presence and color of hair over the area to be treated (if any), and the location of the affected brain region, particularly the depth of the area to be treated relative to the surface. For example, to obtain a desired power density of 50 mW/cm² in the brain at a depth of 3 cm below the surface may require a surface power density of 500 mW/cm². The higher the level of skin pigmentation, the higher the required surface power density to deliver a predetermined power density of light energy to a subsurface brain site. The light energy can have a predetermined power density at the subdermal target tissue (e.g., at a depth of approximately 2 centimeters below the dura). It is presently believed that phototherapy of tissue is most effective when irradiating the target tissue with power densities of light of at least about 0.01 mW/cm² and up to about 1 W/cm². In various embodiments, the subsurface power density is at least about 0.01, 0.05, 0.1, 0.5, 1, 5, 10, 15, 20, 30, 40, 50, 60, 70, 80, or 90 mW/cm², respectively, depending on the desired clinical performance. In certain embodiments, the subsurface power density is preferably about 0.01 mW/cm² to about 100 mW/cm², more preferably about 0.01 mW/cm² to about 50 mW/cm², and most preferably about 2 mW/cm² to about 20 mW/cm². It is believed that these subsurface power densities are especially effective at producing the desired biostimulative effects on the tissue being treated.

The wavelength of the light energy is selected from the range of about 630 µm to about 904 nm, and of course is dependent on the source of light energy used one embodiment, using light apparatus including GaAlAs laser diodes, the light energy has a wavelength of about 830 nm.

In preferred embodiments, the light source used in light therapy is a coherent source (i.e. a laser), and/or the light is substantially monochromatic (i.e. one wavelength or a very narrow band of wavelengths).

To treat a patient, including those suffering from neurodegeneration or a loss or diminishment of motor skills, cognition or cognitive or mental processes or functions, as well as persons having generally normal cognitive or motor functions (whether to enhance such functions or to pre-treat so as to prevent or lessen heat stroke), the light source is placed in contact with a region of skin, for example on the scalp, adjacent a target area of the brain. The target area may be an area of the brain affected by disease or trauma that has been identified such as by using standard medical imaging techniques, it may be a portion of the brain that is known to control certain functions or processes, or it may be any section of the brain, including but not limited to the cortex, cerebellum and other brain regions. Then a surface power density calculation is performed which takes into account factors including skull thickness of the patient, skin coloration, distance to the target site or affected site within the brain, etc. that affect penetration and thus power density at the target or affected site. The power and other parameters are then adjusted according to the results of the calculation.

The precise power density selected for treating the patient will depend on a number of factors, including the specific wavelength of light selected, the type of disease (if any), the clinical condition of the subject including the extent of brain area affected, and the like. Similarly, it should be understood that the power density of light energy to be delivered to the target area or affected brain area may be adjusted to be combined with any other therapeutic agent or agents, especially pharmaceutical agents to achieve the desired biological effect. The selected power density will again depend on a number of factors, including the specific light energy wavelength chosen, the individual additional therapeutic agent or agents chosen, and the clinical condition of the subject.

In preferred embodiments, the treatment proceeds continuously for a period of about 30 seconds to about 2 hours, more preferably for a period of about 1 to 20 minutes. The treatment may be terminated after one treatment period, or the treatment may be repeated with preferably about 1 to 2 days passing between treatments. The length of treatment time and frequency of treatment periods depends on several factors, including the functional recovery of the patient and the results of imaging analysis. In some cases, such as where the disease is degenerative (e.g. Alzheimer's disease) or where treatment is given to a generally healthy patient, the treatment may continue at chosen intervals indefinitely.

During the treatment, the light energy may be continuously provided, or it may be pulsed. If the light is pulsed, the pulses are preferably at least about 10 ns long and occur at a frequency of up to about 100 Hz. Continuous wave light may also be used.

It has been discovered that treatment of stroke using low level light therapy is more effective if treatment begins several hours after the stroke has occurred. This is a surprising result, in that the thrombolytic therapies currently in use for treatment of stroke must begin within a few hours of the stroke. Because oftentimes many hours pass before a person who has suffered a stroke receives medical treatment, the short time limit for initiating thrombolytic therapy excludes many patients from treatment. Consequently, the present methods may be used to treat a greater percentage of stroke patients. Accordingly, it is believed that treatment to enhance cognitive and/or motor function may also take place after a primary event occurs in that it appears that the neural cells need only be living to receive benefit from the methods described herein.

EXAMPLE

An in vitro experiment was done to demonstrate one effect of light therapy on neurons, namely the effect on ATP production. Normal Human Neural Progenitor (NHNP) cells were obtained cryopreserved through Clonetics (Baltimore, Md.), catalog #CC-2599. NHNP cells were thawed and cultured on polyethyleneimine (PEI) with reagents provided with the cells, following the manufacturers instructions. The cells were plated into 96 well plates (black plastic with clear bottoms, Becton Dickinson, Franklin Lakes N.J.) as spheroids and allowed to differentiate into mature neurons over a period of two weeks.

A Photo Dosing Assembly (PDA) was used to provide precisely metered doses of laser light to the NHNP cells in the 96 well plate. The PDA comprised a Nikon Diaphot inverted microscope (Nikon, Melville, N.Y.) with a LUDL motorized x, y, z stage (Ludl Electronic Products, Hawthorne, N.Y.). An 808 nm laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 mm diameter circle when it reached the bottom of the 96 well plate. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nm laser light on the NHNP cells. The first was the CellTiter-Glo Luminescent Cell Viability Assay (Promega, Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems, Sunnyvale, Calif.). Amounts of ATP present in the NHNP cells were quantified in Relative Luminescent Units (RLUs) by the luminometer.

The second assay used was the alamarBlue assay (Biosource, Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices, Sunnyvale, Calif.) was used to measure the absorbance of a well containing NHNP cells, media and alamarBlue diluted 10% v/v. The absorbance of each well was measured at 570 nm and 600 nm and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nm. For the CellTiter-Glo assay, 20 wells were lased for 1 second and compared to an unlased control group of 20 wells. The CellTiter-Glo reagent was added 10 min after lasing completed and the plate was read after the cells had lysed and the luciferase reaction had stabilized. The average RLUs measured for the control wells was 3808+/−3394 while the laser group showed a two fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the twofold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

In one embodiment, treatment of a patient includes implantation of progenitor cells into the central nervous system ("CNS") of the patient. Following implantation, the progenitor cells differentiate to form one or more cell types of the central nervous system. The implanted cells may serve any of a variety of purposes, including replacement of cells or tissues that have been irreparably damaged, repair of a portion of the CNS, enhance the production of important CNS neurochemicals such as dopamine, seratonin, endogenous opioid peptides, and the like. Implantation of progenitor cells may be performed alone, or it may be done in combination with the methods of enhancing neurologic functioning, as described herein.

The term "progenitor cell" as used herein refers to either (1) a pluripotent, or lineage-uncommitted, progenitor cell, a "stem cell" or "mesenchymal stem cell", that is potentially capable of an unlimited number of mitotic divisions to either renew its line or to produce progeny cells that will differentiate into any of a variety of cells, including cells of the central nervous system including neural cells such as astrocytes, oligodendrocytes, and neurons; or (2) a lineage-committed progenitor cell produced from the mitotic division of a stem cell which will eventually differentiate into a neural cell. Unlike the stem cell from which it is derived, the lineage-committed progenitor is generally considered to be incapable of an unlimited number of mitotic divisions and will eventually differentiate into a neural cell or other CNS cell.

The term "differentiation" as used herein refers to the process whereby an unspecialized, pluripotent stem cell proceeds through one or more intermediate stage cellular divisions, ultimately producing one or more specialized cell types. Differentiation thus includes the process whereby precursor cells, i.e. uncommitted cell types that precede the fully differentiated forms but may or may not be true stem cells, proceed through intermediate stage cell divisions to ultimately produce specialized cell types. Differentiation encompasses the process whereby mesenchymal stem cells (MSC) are induced to differentiate into one or more of the committed cell types comprising the central nervous system, in vivo or in vitro.

The terms "growth chamber" and "cell culture chamber" as used herein are used interchangeably and are to be interpreted very broadly to refer to any container or vessel suitable for culturing cells, including, but not limited to, dishes, culture plates (single or multiple well), bioreactors, incubators, and the like. In one embodiment, a cell culture apparatus such as is described in copending U.S. application Ser. No. 10/700,355, filed Nov. 3, 2003 is used. This application is hereby incorporated by reference herein in its entirety.

In a preferred culture method, progenitor cells are inoculated and grown in a cell culture in vitro, using preferred parameters including power density as discussed above. Because the light energy is applied directly to the cell culture in vitro and does not travel through intervening body tissue, the power density selected to be delivered to the cell is generally equal to the power density of the light energy as it is emitted from the light apparatus. If lenses, filters, dispersion gratings, or any other material lies between the light source and the cells, any absorption or dispersion of the light energy by such material should be taken into account and the applied light energy adjusted, if needed, to account for the material. In one embodiment, the treated cells are implanted following treatment. In another embodiment, at least some treated cells remain in culture to maintain the cell line for later use.

After in vitro treatment of cells using electromagnetic energy, the cells are transplanted or implanted to a recipient site in a patient. In one embodiment, the treatment prior to transplantation or implantation includes culturing cells sufficient for implantation. The recipient site may be a site of injury, illness, or defect, or it may be a region of relatively healthy tissue. In some embodiments, the recipient site and/or the region surrounding such site is treated with light energy according to the methods described supra, before and/or after implantation to enhance the rate at which the implanted cells are integrated with surrounding tissue at the recipient site.

In one embodiment, progenitor cells such as stem cells are treated with electromagnetic energy as noted above and then implanted into the brain of a patient, such a patient who is at risk for Parkinson's disease, exhibits symptoms of Parkinson's disease, and/or has been diagnosed with Parkinson's disease. Following implantation, the recipient site is optionally treated with electromagnetic energy, including directly at the recipient site or through the skull at the recipient site, or some other portion of the brain, such as the cortex. The transplanted cells produce dopamine to treat, or lessen the symptoms and/or delay onset of Parkinson's disease in the patient.

In another embodiment, progenitor cells are treated with electromagnetic energy and implanted or transplanted at a site of physical trauma to the spinal cord or one or more nerves of a patient. Following implantation, the recipient site is optionally treated with electromagnetic energy. Such optional treatment may include treatment immediately following implantation and/or one or more treatment periods following implantation. The transplanted cells help repair damage to the spinal cord or nerve(s) such that the recovery or prognosis is enhanced in patients having implanted progenitor cells as compared with those who do not receive such implants.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for enhancing neurologic function in a subject, said method comprising:
   providing a subject having a loss of neurologic function due to Parkinson's disease or Alzheimer's disease; and
   noninvasively delivering a neurologic function enhancing effective amount of light energy having a wavelength in the visible to near-infrared wavelength range and a predetermined power density to the brain of the subject, wherein noninvasively delivering the neurologic function enhancing effective amount of light energy comprises transmitting light energy through the scalp and the skull to the brain, wherein the predetermined power density is at least about 0.01 mW/cm$^2$ at a depth of approximately 2 centimeters below the dura.

2. A method according to claim 1, wherein the predetermined power density is selected from the range of about 0.01 mW/cm$^2$ to about 100 mW/cm$^2$ at a depth of approximately 2 centimeters below the dura.

3. A method according to claim 2 wherein the predetermined power density is selected from the range of about 0.01 mW/cm$^2$ to about 15 mW/cm$^2$ at a depth of approximately 2 centimeters below the dura.

4. A method according to claim 1, wherein the light energy has a wavelength of about 630 nm to about 904 nm.

5. A method according to claim 4 wherein the light energy has a wavelength of about 780 nm to about 840 nm.

6. A method according to claim 1 wherein delivering a neurologic function enhancing effective amount of light energy to the brain comprises placing a light source in contact with a region of skin adjacent to the brain.

7. A method according to claim 1, wherein delivering light energy comprises determining a surface power density of the light energy sufficient to deliver the predetermined power density of light energy to the brain.

8. A method according to claim 7 wherein determining a surface power density of the light energy sufficient to deliver the predetermined power density of light energy to the brain comprises determining the surface power density of the light energy sufficient for the light energy to traverse the distance between the skin surface and the brain.

9. A method according to claim 8 wherein determining the surface power density further comprises determining the surface power density sufficient to penetrate the skull.

10. A method according to claim 1, wherein the treatment proceeds for a period of about 30 seconds to about 2 hours.

11. A method according to claim 1, wherein the light energy is pulsed.

12. A method of increasing neurologic function by increasing the production of ATP by neurons, comprising:
   noninvasively irradiating neurons of a subject having a loss of neurologic function due to Parkinson's disease or Alzheimer's disease with light energy with a predetermined power density and having a wavelength in the near infrared to visible portion of the electromagnetic spectrum for at least about 1 second;

wherein the predetermined power density of said light energy at the neurons is at least about 0.01 mW/cm$^2$ at a depth of approximately 2 centimeters below the dura, whereby the ATP production of neurons is increased.

13. A method according to claim 12 wherein the predetermined power density is selected from the range of about 0.01 mW/cm$^2$ to about 100 mW/cm$^2$ at a depth of approximately 2 centimeters below the dura.

14. A method according to claim 13 wherein the predetermined power density is less than about 15 mW/cm$^2$ at a depth of approximately 2 centimeters below the dura.

15. A method according to claim 12 wherein the light energy has a wavelength of about 630 nm to about 904 nm.

16. A method according to claim 15 wherein the light energy has a wavelength of about 780 nm to about 840 nm.

17. A method according to claim 12, wherein the light energy is pulsed.

18. A method for enhancing neurologic function in a subject, said method comprising:

noninvasively delivering a neurologic function enhancing effective amount of light energy through the scalp and the skull to the brain of a subject having a loss of neurologic function due to Parkinson's disease or Alzheimer's disease, the light energy having a wavelength in the visible to near-infrared wavelength range and a predetermined power density to the brain of at least about 0.01 mW/cm$^2$ at a depth of approximately 2 centimeters below the dura.

19. A method according to claim 18, wherein the predetermined power density is selected from the range of about 0.01 mW/cm$^2$ to about 100 mW/cm$^2$ at a depth of approximately 2 centimeters below the dura.

20. A method according to claim 18, wherein the light energy has a wavelength of about 780 nm to about 840 nm.

21. A method according to claim 18, wherein noninvasively delivering a neurologic function enhancing effective amount of light energy comprises placing a light source in contact with a region of skin adjacent to the brain.

22. A method according to claim 18, wherein the light energy is pulsed.

* * * * *

UNITED STATES PATENT AND TRADEMARK OFFICE
CERTIFICATE OF CORRECTION

PATENT NO. : 7,534,255 B1  Page 1 of 1
APPLICATION NO. : 10/764986
DATED : May 19, 2009
INVENTOR(S) : Jackson Streeter and Luis De Taboada It is certified that error appears in the above-identified patent and that said Letters Patent is hereby corrected as shown below:

On the Title Page, Item (56), page 2 (Other Publications), line 62, please delete "Laster Irradation ar eMore", and insert -- Laser Irradiation are More --, therefor.

Item (56), page 3 (Other Publications), line 22, please delete "Michondrial", and insert -- Mitochondrial --, therefor.

Item (56), page 3 (Other Publications), line 2, please delete "Geme", and insert -- Gene --, therefor.

At column 6, line 14, please delete "amylotrophic", and insert -- amyotrophic --, therefor.

At column 10, line 46, please delete "seratonin,", and insert -- serotonin, --, therefor.

Signed and Sealed this

Twenty-sixth Day of January, 2010

David J. Kappos
*Director of the United States Patent and Trademark Office*